US011707547B2

(12) United States Patent
Fiorello et al.

(10) Patent No.: US 11,707,547 B2
(45) Date of Patent: Jul. 25, 2023

(54) STERILIZATION TEST DEVICE

(71) Applicant: American Sterilizer Company, Mentor, OH (US)

(72) Inventors: Anthony J. Fiorello, Mentor, OH (US); Christopher J. Lannan, Painesville, OH (US)

(73) Assignee: American Sterilizer Company, Mentor, OH (US)

( * ) Notice: Subject to any disclaimer, the term of this patent is extended or adjusted under 35 U.S.C. 154(b) by 346 days.

(21) Appl. No.: 16/876,727

(22) Filed: May 18, 2020

(65) Prior Publication Data
US 2021/0353810 A1    Nov. 18, 2021

(51) Int. Cl.
*A61L 2/28* (2006.01)
*A61L 2/07* (2006.01)

(52) U.S. Cl.
CPC .................. *A61L 2/28* (2013.01); *A61L 2/07* (2013.01); *A61L 2202/121* (2013.01); *A61L 2202/122* (2013.01); *A61L 2202/26* (2013.01)

(58) Field of Classification Search
CPC ........ A61L 2/28; A61L 2/07; A61L 2202/121; A61L 2202/122; A61L 2202/26; A61L 2/20; A61L 2/206; A61L 2/208
See application file for complete search history.

(56) References Cited

U.S. PATENT DOCUMENTS

| 4,596,696 | A | * | 6/1986 | Scoville, Jr. | ............... A61L 2/28 435/31 |
| 1,914,034 | A | | 4/1990 | Welsh | |
| 5,968,807 | A | * | 10/1999 | Kaiser | ................... C12M 23/32 435/31 |
| 7,790,105 | B2 | | 9/2010 | Bala | |
| 9,017,994 | B2 | | 4/2015 | Franciskovich et al. | |
| 2011/0211991 | A1 | * | 9/2011 | Foltz | ........................ A61L 2/28 422/119 |
| 2013/0273594 | A1 | * | 10/2013 | Ahimou | ................... A61L 2/28 435/31 |
| 2019/0307910 | A1 | | 10/2019 | Bala | |

FOREIGN PATENT DOCUMENTS

| WO | 2019195683 A1 | 10/2019 |
| WO | 2020023833 A1 | 1/2020 |

OTHER PUBLICATIONS

International Search Report issued by ISA/EP in connection with PCT/US2021/031941 dated Sep. 3, 2021.
Written Opinion of the International Searching Authoriy issued by ISA/EP in connection with PCT/US2021/031941 dated Sep. 3, 2021.
International Preliminary Report on Patentability issued by WIPO in connection with PCT/US2021/031941 dated Dec. 1, 2022.

* cited by examiner

*Primary Examiner* — Sean E Conley
*Assistant Examiner* — Brendan A Hensel
(74) *Attorney, Agent, or Firm* — Levenfeld Pearlstein, LLC

(57) ABSTRACT

A sterilization process test device for verifying the efficacy of a sterilization process includes a tubular body defining a chamber for containing at least one sterilization indicator and a cap to sealingly close the tubular body. The tubular body includes at least one hole, which is covered by a gas and steam permeable cover. The only flow path into the chamber is provided through the steam and gas permeable cover and the at least one hole, which when combined are configured to control and restrict a flow of steam or a gaseous sterilization medium from an external environment.

13 Claims, 1 Drawing Sheet

STERILIZATION TEST DEVICE

BACKGROUND

The present invention is directed to a sterilization test device for verifying the efficacy of a sterilization process.

The sterilization of medical equipment, towels (for hospital and operating room use), gowns and the like is carried out, for the most part, using steam sterilization equipment and methods. For example, a bundle of towels is placed into a steam sterilizer, a vacuum is drawn in the sterilizer to evacuate the air, and steam is introduced to sterilize the bundle of towels.

Due to the nature of the towels being "bundled" it may be difficult to assure that the innermost regions of the towels have been sufficiently subjected to the steam to assure proper levels of sterilization. Essentially, it is a "challenge" for the steam to be introduced to the innermost parts to effect sterilization.

To this end, "challenge packs" or "challenge kits" have been developed to simulate the bundle and more specifically to simulate the difficulty or resistance in reaching the innermost parts: (1) to effect a vacuum; and (2) to introduce steam sufficient to sterilize the local area. There is in fact an ANSI standard for challenge packs that is based upon a bundle of towels having a specific size.

Presently, there are challenge packs on the market. These include paper stacks (stacked like a deck of cards) with an indicator sheet generally in the middle of the stack that can indicate either that a vacuum has been achieved or that a sufficient amount of steam has reached the indicator pack. Another includes a paper stack with a cut out center with a biological indicator vile in the middle. Still another type of indicator includes a plastic container that has a hole in one end, is packed with a permeable material (such as a towel or absorbent paper sheet) and an indicator at the opposite end.

U.S. Pat. No. 9,017,994, which is assigned to the Applicant of the present application and incorporated herein by reference, discloses a sterilization test pack including at least one channel configured to provide a restricted flow path(s) to biological and chemical indicators, in which the at least one channel is defined by a groove(s) or indentation(s) having a depth, a width, and a length. US Patent Application Publication No. 2019/0307910, which is also assigned to the Applicant of the present application and incorporated herein by reference, discloses a sterilization process challenge device comprising a filter assembly that includes filter members and gaskets to provide a restrictive fluid flow path into a challenge device chamber. Further, U.S. Pat. No. 7,790,105, which is also assigned to the Applicant of the present application and incorporated herein by reference, discloses a sterilization challenge specimen holder including a holder configured to hold a sterilization indicator, such as a biological indicator, and a plug including grooves configured to provide a restricted flow path(s) to the sterilization indicator.

Accurate and cost effective verification of sterilization processes is important for obvious reasons. The present disclosure provides a cost effective sterilization process test device that closely mimics the challenge to reach the innermost regions of a bundle of towels used in the ANSI/AAMI ST79 for sterilization challenge packs.

BRIEF SUMMARY

In one aspect, a sterilization process test device comprising a body defining a chamber configured to contain at least one sterilization indicator, a cap and a steam and gas permeable cover is provided. The body may include an inlet opening for receiving the at least one sterilization indicator and at least one hole, wherein each of the at least one hole may be defined by an opening extending through a thickness of the body. The cap may be configured to engage the body to sealingly close the inlet opening. The steam and gas permeable cover may be arranged over the at least one hole and attached to an outer surface of the body surrounding the at least one hole. The sterilization process test device may be configured such that the only fluid communication between the chamber and an external environment is provided through the steam and gas permeable cover and the at least one hole.

In some embodiments, each of the at least one hole may be defined by a generally circular shaped opening having a diameter of less than 0.1 inches. For example, each of the at least one hole may be defined by a generally circular shaped opening having a diameter of about $1/16$ inches to about $3/32$ inches. In an embodiment, the at least one hole may include a single hole defined by a generally circular shaped opening having a diameter of about $1/16$ inches. In another embodiment, the at least one hole may include two holes, each defined by a generally circular shaped opening having a diameter of about $1/16$ inches. In yet another embodiment, the at least one hole may include four holes, each defined by a generally circular shaped opening having a diameter of about $1/16$ inches. In an embodiment, the at least one hole may include one hole defined by a generally circular shaped opening having a diameter of about $3/32$ inches.

In an embodiment, the steam and gas permeable cover may be formed from a crepe paper having a basis weight of about 35 GSM to about 55 GSM, a porosity of about 15 Gurley Seconds to about 25 Gurley Seconds when tested according to Tappi T-460, and a thickness of about 4.5 mil to about 7 mil. In another embodiment, the steam and gas permeable cover may be formed from an autoclave tape comprising a crepe paper substrate and an adhesive layer, wherein the autoclave tape has a total thickness of about 5.5 mil to about 6 mil.

In some embodiments, the cap may be formed from silicone. The body may have a generally tubular shape and configured to withstand the heat and vacuum pressure during a steam sterilization process. In an embodiment, the body may be a tubular body formed from polycarbonate and having a thickness of about $1/16$ inches to about $1/4$ inches. For example, the body may be a tubular body formed from polycarbonate and having an outer diameter of about $3/4$ inches, an inner diameter of about $5/8$ inches, and a length of about 3.75 inches.

In an embodiment, the at least one sterilization indicator may include a biological indicator and a chemical indicator. In such an embodiment, the sterilization process test device may be configured to exhibit fail conditions after a sterilization process cycle at 132° F. for 4 minutes and exhibit pass conditions after a sterilization process cycle at 132° F. for 10 minutes cycle. The fail conditions include a positive biological indicator result, which indicates at least some microorganisms in the biological indicator survived the sterilization process cycle at 132° F. for 4 minutes, and a fail chemical indicator result indicating that the chemical indicator did not reach an endpoint color after the sterilization process cycle at 132° F. for 4 minutes. The pass conditions include a negative biological indicator result, which indicates all microorganisms in the biological indicator were killed during the sterilization process cycle at 132° F. for 10 minutes and a pass chemical indicator result indicating that the chemical indicator reached an endpoint color after the sterilization process cycle at 132° F. for 10 minutes.

Other aspects, objectives and advantages will become more apparent from the following detailed description.

BRIEF DESCRIPTION OF THE SEVERAL VIEWS OF THE DRAWINGS

The benefits and advantages of the present invention will become more readily apparent to those of ordinary skill in the relevant art after reviewing the following detailed description and accompanying drawings, wherein.

For simplicity and clarity of illustration, elements shown in the figures may not be drawn to scale. For example, the dimension of some of the elements may be exaggerated relative to each other for clarity.

DETAILED DESCRIPTION

While the present disclosure is susceptible of embodiment in various forms, there will hereinafter be described presently preferred embodiments with the understanding that the present disclosure is to be considered an exemplification and is not intended to limit the disclosure to the specific embodiments illustrated.

It should be further understood that the title of this section of this specification, namely, "Detailed Description", relates to a requirement of the United States Patent Office, and does not imply, nor should be inferred to limit the subject matter disclosed herein.

A sterilization process test device according to various embodiments is provided. The test device may be configured to hold a biological indicator and/or a chemical indicator to test the efficacy of a sterilization process. For example, the test device may be used to verify the efficacy of a sterilization process involving steam or gaseous sterilization medium/sterilants, such as gaseous hydrogen peroxide, gaseous ethylene oxide, and the like. The biological indicator may contain microorganisms, such as *Escherichia coli, Legionella* sp., *Campylobacter* sp., *Staphylococcus, Streptococcus* species and *Cryptosporidium.*

Figure 1:
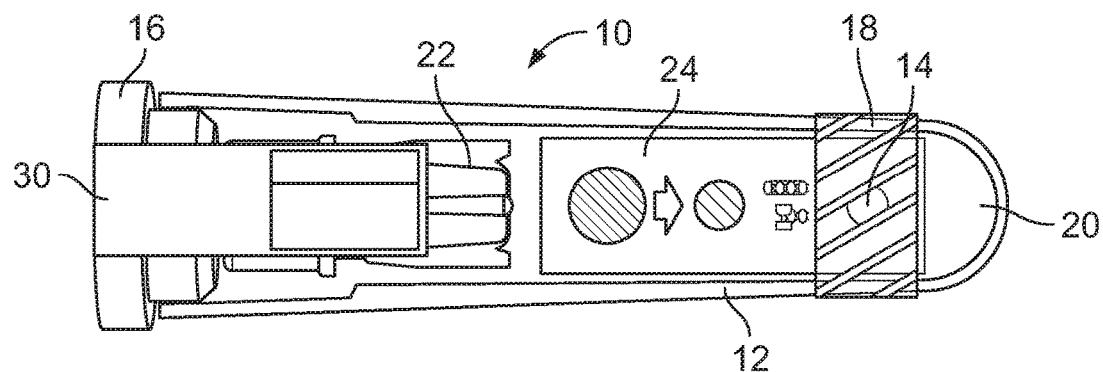
FIG. 1 is a perspective view of a sterilization process test device according to an embodiment.
Figure 2:
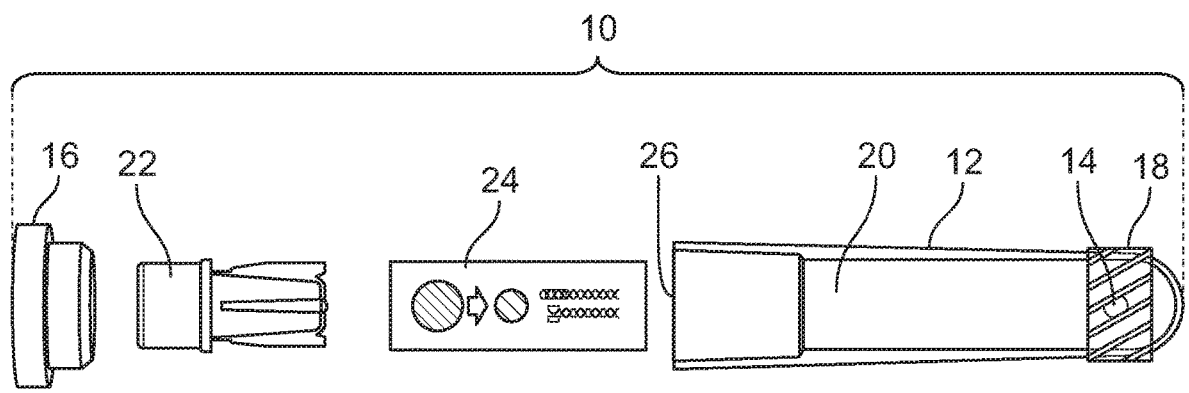
FIG. 2 is an exploded view of the test device of FIG. 1.

FIGS. 1 and 2 illustrate a sterilization process test device 10 according to an embodiment. FIG. 1 shows the test device 10 as assembled and ready for use in a sterilization process cycle, and FIG. 2 is an exploded view of the test device 10. The test device 10 may generally comprise a tubular body 12 including at least one hole 14, a cap 16, and a steam and gas permeable cover 18 attached to the tubular body 12 to cover the at least one hole 14. The tubular body 12 may define a chamber 20 configured to hold a biological indicator 22 and/or a chemical indicator 24. In this embodiment, the test device 10 includes the tubular body 12 having a generally cylindrical shaped body. In other embodiments, the test device may include a various shaped body comprising a chamber for holding a biological indicator and/or a chemical indicator, for example, a generally rectangular shaped body.

The cap 16 may be configured to sealingly engage a peripheral portion of the tubular body 12 to close and seal an inlet opening 26 of the chamber 20. The cap 16 may be formed from a suitable material, such as silicone, elastomer, and the like. The cap 16 and the tubular body 12 may be configured to provide a fluid tight seal when engaged with each other, such that an only fluid flow path from an external environment into the chamber 20 is provided through the at least one hole 14. The chamber 20 may be sized and configured to hold a biological indicator 22 and/or a chemical indicator 24. For example, the chamber 20 may contain a biological indicator 22, such as a self-contained biological indicator (SCBI) and/or a chemical indicator 24.

The at least one hole 14 may be configured to provide a flow path to allow steam or gaseous sterilization medium/sterilants to flow into the chamber 20. In the embodiment of FIGS. 1 and 2, the test device 10 includes one hole 14 arranged proximate a distal end of the tubular body 12 opposite the inlet opening 26, wherein the hole 14 may be defined by a generally circular opening extending through a thickness of the tubular body 12. The circular hole 14 may have a diameter of less than about 0.1 inches, preferably about 1/32 inches to about 0.1 inches, more preferably about 1/16 inches to about 3/32 inches. In other embodiments, the test device 10 may include more than one hole. For example, the test device 10 may include two holes, three holes, four holes, five holes, six holes, seven holes, eight holes, nine holes, ten holes, eleven holes, or twelve holes, wherein each of the holes may be defined by a generally circular opening extending through a thickness of the tubular body 12 and having a diameter of less than about 0.1 inches, preferably about 1/32 inches to about 0.1 inches, and more preferably about 1/16 inches to about 3/32 inches.

In some embodiments, each of the at least one hole 14 may be defined by openings of various shapes, for example, square openings, rectangular openings, diamond openings, star-shaped openings, and the like, wherein each of the openings has an area of less than about 0.03 square inch (in$^2$), preferably about 0.012 in$^2$ to about 0.27 in$^2$. The at least one hole 14 may be arranged at various locations on the tubular body 12. For example, the at least one hole 14 may be arranged proximate a center portion of the tubular body 12 or proximate the inlet opening 26 of the tubular body 12.

The at least one hole 14 may be covered by the steam and gas permeable cover 18, such that a flow path into the chamber 20 may be defined through the steam and gas permeable cover 18 and the at least one opening 14. The steam and gas permeable cover 18 may be arranged over the at least one hole 14 and sealed to an outer surface of the tubular body 12 surrounding the at least one hole 14, such that steam or gaseous sterilization medium/sterilants may flow through the steam and gas permeable cover 18 and the at least one hole 14 without bypassing the steam and gas permeable cover 18. In an embodiment, the steam and gas permeable cover 18 may be arranged such that the at least one hole 14 is proximately adjacent the center of the steam and gas permeable cover 18. The steam and gas permeable cover 18 may be configured to completely cover the at least one hole 14 and extend therebeyond to provide a bonding area sufficient for maintaining the steam and gas permeable cover 18 attached to the tubular body 12 throughout a sterilization process. In an embodiment, the steam and gas permeable cover 18 may have a width of about 0.5 inches to about 2 inches, preferably about 1 inch to about 1.5 inches, and a length of about 1 inch to about 5 inches, preferably about 2 inches to about 4 inches. For example, the steam and gas permeable cover 18 may have a width of about 1 inch and a length of about 2.5 inches or a width of about 1 inch and a length of about 3 inches.

When attached to the tubular body 12 to cover the at least one hole 14, the steam and gas permeable cover 18 together with the at least one hole 14 may be configured to provide a desired flow restriction into the chamber 20. For example, the at least one hole 14 and the steam and gas permeable cover 18 may be configured to provide a flow restriction that closely mimic the challenge to reach the innermost regions of a bundle of towels used in the ANSI/AAMI ST79 for sterilization challenge packs.

The steam and gas permeable cover 18 may be formed from a suitable porous material. Suitable materials for the steam and gas permeable cover 18 may include, but are not limited to, a crepe paper, filter media, nonwoven, and the like. For example, the steam and gas permeable cover 18 may be formed from a crepe paper having a basis weight of about 25 grams per square meter (GSM) to about 65 GSM, preferably about 35 GSM to about 55 GSM, and more preferably about 47 GSM, and a porosity of about 10 Gurley Seconds (when tested according to Tappi T-460, 2 ply, 400 cc) to about 30 Gurley Seconds, preferably about 15 Gurley Seconds to about 25 Gurley Seconds, and more preferably about 18 Gurley Seconds, and a thickness of about 3.5 mil to about 8 mil (when tested according to Tappi T-411), preferably about 4.5 mil to about 7 mil, and more preferably about 5.8 mil. In an embodiment, the steam and gas permeable cover 18 may comprise a porous substrate layer and an adhesive layer configured to adhere to the tubular body 12. For example, the steam and gas permeable cover 18 may be formed from an autoclave tape suitable for a steam sterilization process. In an embodiment, the steam and gas permeable cover 18 may be formed from an autoclave tape comprising a crepe paper substrate and an adhesive layer and having a total thickness of about 5.5 mil to about 6 mil, such as Cantech® 146, Cantech® 147, or Cantech® 144C Process Indicator Tape for Steam Sterilization available from Intertape Polymer Inc. or Fisherbrand™ Lead-Free Autoclave Tape available from Fisher Scientific.

In another embodiment, the steam and gas permeable cover 18 may be formed from a suitable filter material having a micron rating of about 1.0 to about 4 micron, preferably about 1.5 to 2.5 micron. Examples of the suitable filter material include, but are not limited to, a binder-free microfiber glass filter having a micron rating of 1.0, such as Ahlstrom™ Grade 121, an ashless, cotton filter having a micron rating of 1.5, such as Ahlstrom™ Grade 94, a white, smooth surface, cotton filter having a micron rating of 1.5, such as Ahlstrom™ Grade 610, a white, smooth surface, cotton filter having a micron rating of 2.0, such as Ahlstrom™ Grade 642, a white, smooth surface, cotton filter having a micron rating of 2.5, such as Ahlstrom™ Grade 601, and a white, smooth surface, cotton filter having a micron rating of 3.0, such as Ahlstrom™ Grade 238.

The tubular body 12 may be formed from a suitable polymeric material and configured to withstand the heat and vacuum pressure during a steam sterilization process without collapsing and/or melting. Suitable polymeric materials may include, but are not limited to, polypropylene, polycarbonate, polyester, polyolefin, polystyrene, polyacrylamide, polymethacrylate, poly(methyl)methacrylate, polyimide, polyethylene terephthalate, polybutylene terephthalate, polyvinylchloride, or other similar polymers. In an embodiment, the tubular body 12 may be formed from polycarbonate and have a wall thickness of about 1/16 inches to about 1/4 inches, preferably about 1/8 inches.

In an embodiment, the test device 10 may include a chemical indicator 24 and may be configured such that the chemical indicator 24 is visible from outside to allow a user may check the chemical indicator 24 without removing the cap 16. In such an embodiment, the tubular body 12 may be formed from a substantially clear plastic material to facilitate viewing of the chemical indicator from outside the test device 10.

In an embodiment, the test device 10 may be prepared by placing a biological indicator 22 and a chemical indicator 24 in the chamber 20 and sealing the tubular body 12 with the cap 16. A tamper-evident seal label 30 may be attached over the cap 16 and the tubular body 12 as shown in FIG. 1.

In use, the test device 10 may be placed in a sterilization equipment along with the objects to be sterilized. During a sterilization process cycle, steam or other gaseous sterilization medium may flow into the chamber 20 through the steam and gas permeable cover 18 and the at least one hole 14, wherein the flow of the steam or gaseous sterilization medium is restricted by the steam and gas permeable cover 18 and the at least one hole 14. In some sterilization processes, a vacuum may be drawn in the sterilization equipment (and thus in the sterilization test device 10), following which the steam or sterilization medium is introduced into the equipment (and thus the test device 10.) The steam or gaseous sterilization medium may then permeate into the biological indicator 22 and/or the chemical indicator 24. At the end of the sterilization process cycle, a user may open the cap 16 to remove the biological indicator 22 and chemical indicator 24 to evaluate the efficacy of the sterilization process. The test device 10 may be configured such that the flow of steam or other gaseous sterilization medium may be restricted by the steam and gas permeable cover 18 and the at least one hole 14 to closely mimic the flow resistance into the center of 16-towel test pack used in the ANSI/AAMI ST79 for sterilization challenge packs.

Some prior art challenge packs include relatively complex assemblies and/or components, such as an absorber or other sterilant-reactive device, to restrict the flow of steam or gaseous sterilization medium, which may require relatively complex manufacturing steps and/or relatively expensive materials. The test device according to various embodiments of the present disclosure is relatively simple and cost effective to make and may be configured to provide the restrictive flow path that closely mimics that of the 16-towel pack. As such, the test device of the present disclosure may be provided as disposable sterilization process test devices.

Samples of the sterilization process test device 10 of FIGS. 1 and 2 were prepared and tested to evaluate the performance of the test device. The test device samples comprised a tubular body 12 formed from polycarbonate and having a outer diameter of about 3/4 inches, an inner diameter of about 5/8 inches, and a length of about 3.75 inches. The test device samples included at least one hole 14 proximate a distal end of the tubular body 12. Some test device samples included one hole defined by a generally circular opening having a diameter of about 1/16 inches, 3/32 inches, or 9/64 inches. Some test device samples included two holes or four holes, each of the holes defined by a generally circular opening having a diameter of about 1/16 inches. The steam and gas permeable cover 18 having a width of about 1 inch and a length of about 2.5 inches and formed from a Cantech® 144C Lead-Free Autoclave Tape for Steam Sterilization or Fisherbrand™ Lead-Free Autoclave Tape was attached to the tubular body 12 to cover the at least one hole 14. A Celerity™ Steam Biological Indicator (LCB048) available from Steris and a Celebrity™ 10 Steam Chemical Indicator (PCC076) for a 132° C./4 minute steam sterilization cycle available for Steris were placed in the chamber 20. The tubular body 12 was then sealingly closed with the cap 16 formed from silicone. The test device samples were place in a steam sterilization equipment for a sterilization process cycle at 132° F. for 4 minutes (min), 5 min, 6 min, 8 min, or 10 min and evaluated for sterilization process challenge characteristics. Test results are shown in Table 1.

TABLE 1

Sterilization Test Device Evaluation

| Sample Number | Tape | Tape Lot | Number of Holes | Each Hole Size (inch) | Exposure Time (Min) | Biological Indicator Result | Chemical Indicator Result |
|---|---|---|---|---|---|---|---|
| 1 | Cantech 144C | 144-00c | 1 | 9/64 | 4 | Negative | Pass |
| 2 | Cantech 144C | 144-00c | 1 | 3/32 | 4 | Positive | Fail |
| 3 | Cantech 144C | 144-00c | 1 | 1/16 | 4 | Positive | Fail |
| 4 | Cantech 144C | 144-00c | 2 | 1/16 | 4 | Positive | Fail |
| 5 | Cantech 144C | 144-00c | 4 | 1/16 | 4 | Positive | Fail |
| 6 | Cantech 144C | 144-00c | 1 | 9/64 | 6 | Negative | Pass |
| 7 | Cantech 144C | 144-00c | 1 | 3/32 | 6 | Negative | Pass |
| 8 | Cantech 144C | 144-00c | 1 | 1/16 | 6 | Positive | Fail |
| 9 | Cantech 144C | 144-00c | 2 | 1/16 | 6 | Negative | Pass |
| 10 | Cantech 144C | 144-00c | 4 | 1/16 | 6 | Negative | Pass |
| 11 | Cantech 144C | 144-00c | 1 | 9/64 | 8 | Negative | Pass |
| 12 | Cantech 144C | 144-00c | 1 | 3/32 | 8 | Negative | Pass |
| 13 | Cantech 144C | 144-00c | 1 | 1/16 | 8 | Negative | Pass |
| 14 | Cantech 144C | 144-00c | 2 | 1/16 | 8 | Negative | Pass |
| 15 | Cantech 144C | 144-00c | 4 | 1/16 | 8 | Negative | Pass |
| 16 | Cantech 144C | 144-00c | 1 | 9/64 | 10 | Negative | Pass |
| 17 | Cantech 144C | 144-00c | 1 | 3/32 | 10 | Negative | Pass |
| 18 | Cantech 144C | 144-00c | 1 | 1/16 | 10 | Positive | Fail |
| 19 | Cantech 144C | 144-00c | 2 | 1/16 | 10 | Negative | Pass |
| 20 | Cantech 144C | 144-00c | 4 | 1/16 | 10 | Negative | Pass |
| 21 | Fisherbrand | 917709 | 1 | 9/64 | 4 | Positive | Fail |
| 22 | Fisherbrand | 917709 | 1 | 3/32 | 4 | Positive | Fail |
| 23 | Fisherbrand | 917709 | 1 | 1/16 | 4 | Positive | Fail |
| 24 | Fisherbrand | 917709 | 2 | 1/16 | 4 | Positive | Fail |
| 25 | Fisherbrand | 917709 | 4 | 1/16 | 4 | Positive | Fail |
| 26 | Fisherbrand | 917709 | 1 | 9/64 | 10 | Negative | Pass |
| 27 | Fisherbrand | 917709 | 4 | 1/16 | 10 | Negative | Pass |
| 28 | Fisherbrand | 917709 | 1 | 3/32 | 10 | Negative | Pass |
| 29 | Fisherbrand | 917709 | 1 | 1/16 | 10 | Negative | Pass |
| 30 | Fisherbrand | 917709 | 2 | 1/16 | 10 | Negative | Pass |
| 31 | Fisherbrand | 917709 | 1 | 9/64 | 6 | Negative | Pass |
| 32 | Fisherbrand | 917709 | 4 | 1/16 | 6 | Positive | Fail |
| 33 | Fisherbrand | 917709 | 1 | 3/32 | 6 | Positive | Fail |
| 34 | Fisherbrand | 917709 | 1 | 1/16 | 6 | Positive | Fail |
| 35 | Fisherbrand | 917709 | 2 | 1/16 | 6 | Positive | Fail |
| 36 | Fisherbrand | 917709 | 1 | 9/64 | 8 | Negative | Pass |
| 37 | Fisherbrand | 917709 | 4 | 1/16 | 8 | Positive | Fail |
| 38 | Fisherbrand | 917709 | 1 | 3/32 | 8 | Negative | Pass |
| 39 | Fisherbrand | 917709 | 1 | 1/16 | 8 | Positive | Fail |
| 40 | Fisherbrand | 917709 | 2 | 1/16 | 8 | Positive | Fail |
| 41 | Fisherbrand | 917709 | 1 | 9/64 | 5 | Negative | Pass |
| 42 | Fisherbrand | 917709 | 1 | 3/32 | 5 | Positive | Fail |
| 43 | Fisherbrand | 917709 | 1 | 1/16 | 5 | Positive | Fail |
| 44 | Fisherbrand | 917709 | 2 | 1/16 | 5 | Positive | Fail |
| 45 | Fisherbrand | 917709 | 4 | 1/16 | 5 | Positive | Fail |
| 46 | Fisherbrand | 917709 | 1 | 3/32 | 4 | Positive | Fail |
| 47 | Fisherbrand | 917709 | 1 | 1/16 | 4 | Positive | Fail |
| 48 | Fisherbrand | 917709 | 2 | 1/16 | 4 | Positive | Fail |
| 49 | Fisherbrand | 917709 | 4 | 1/16 | 4 | Positive | Fail |
| 50 | Fisherbrand | 917709 | 1 | 9/64 | 4 | Negative | Pass |
| 51 | Fisherbrand | 917812 | 1 | 9/64 | 10 | Negative | Pass |
| 52 | Fisherbrand | 917812 | 4 | 1/16 | 10 | Negative | Pass |
| 53 | Fisherbrand | 917812 | 1 | 3/32 | 10 | Negative | Pass |
| 54 | Fisherbrand | 917812 | 1 | 1/16 | 10 | Positive | Fail |
| 55 | Fisherbrand | 917812 | 2 | 1/16 | 10 | Negative | Pass |
| 56 | Fisherbrand | 917812 | 1 | 3/32 | 4 | Positive | Fail |
| 57 | Fisherbrand | 917812 | 1 | 1/16 | 4 | Positive | Fail |
| 58 | Fisherbrand | 917812 | 2 | 1/16 | 4 | Positive | Fail |
| 59 | Fisherbrand | 917812 | 4 | 1/16 | 4 | Positive | Fail |
| 60 | Fisherbrand | 917812 | 1 | 9/64 | 4 | Positive | Fail |
| 61 | Fisherbrand | 917812 | 1 | 3/32 | 6 | Positive | Fail |
| 62 | Fisherbrand | 917812 | 1 | 1/16 | 6 | Positive | Fail |
| 63 | Fisherbrand | 917812 | 2 | 1/16 | 6 | Negative | Pass |
| 64 | Fisherbrand | 917812 | 4 | 1/16 | 6 | Negative | Pass |
| 65 | Fisherbrand | 917812 | 1 | 9/64 | 6 | Negative | Pass |
| 66 | Fisherbrand | 917812 | 1 | 9/64 | 8 | Negative | Pass |
| 67 | Fisherbrand | 917812 | 1 | 3/32 | 8 | Negative | Pass |
| 68 | Fisherbrand | 917812 | 1 | 1/16 | 8 | Positive | Fail |
| 69 | Fisherbrand | 917812 | 2 | 1/16 | 8 | Negative | Pass |
| 70 | Fisherbrand | 917812 | 4 | 1/16 | 8 | Negative | Pass |

The test device samples that exhibit fail conditions after a sterilization process cycle at a 132° F. for 4 minutes and pass conditions after a sterilization process cycle at a 132° F. for 10 minutes were considered to provide a sterilization process challenge comparable to the restrictive flow path into the center of 16-towel test pack used in the ANSI/AAMI ST79 for sterilization challenge packs. The fail conditions included a positive biological indicator result indicating that at least some microorganisms in the biological indicator survived the steam sterilization process cycle and a fail chemical indicator result indicating that the chemical indicator did not reach an endpoint color. The pass conditions included a negative biological indictor result indicating that all microorganisms were killed during a steam sterilization process cycle and a pass chemical indicator result indicating that the chemical indicator reached the endpoint color. The test results showed that the test device samples including one hole having a diameter of greater than 0.1 inches, for example, Samples 1 and 50, exhibited pass conditions after a sterilization process cycle at 132° F. for 4 minutes, which indicated that the test device samples failed to provide a sufficient sterilization process challenge to mimic the 16-towel pack. The test results also showed that the test device samples including one hole, two holes or four holes, wherein each of the holes had a diameter of less than about 1 inch, exhibited fail conditions after a sterilization process cycle at 132° F. for 4 minutes while exhibiting pass conditions after a sterilization process cycle at a 132° F. for 10 minutes to indicate that the test device samples provided a sufficient flow resistance to mimic the flow resistance to reach the center of the 16-towel pack.

All patents referred to herein, are hereby incorporated herein in their entirety, by reference, whether or not specifically indicated as such within the text of this disclosure.

In the present disclosure, the words "a" or "an" are to be taken to include both the singular and the plural. Conversely, any reference to plural items shall, where appropriate, include the singular.

From the foregoing it will be observed that numerous modifications and variations can be effectuated without departing from the true spirit and scope of the novel concepts of the present disclosure. It is to be understood that no limitation with respect to the specific embodiments illustrated is intended or should be inferred. The disclosure is intended to cover by the appended claims all such modifications as fall within the scope of the claims.

What is claimed is:

1. A sterilization process test device, comprising:
a body including a chamber configured to contain at least one sterilization indicator, an inlet opening configured to receive the at least one sterilization indicator, and at least one hole, wherein each of the at least one hole is defined by an opening extending through a thickness of the body;
a cap configured to engage the body to sealingly close the inlet opening; and
a steam and gas permeable cover arranged over the at least one hole and attached to an outer surface of the body surrounding the at least one hole;
wherein the only fluid communication between the chamber and an external environment is provided through the steam and gas permeable cover and the at least one hole,
wherein the steam and gas permeable cover is formed from a crepe paper having a basis weight of about 35 GSM to about 55 GSM, a porosity of about 15 Gurley Seconds to about 25 Gurley Seconds when tested according to Tappi T-460, and a thickness of about 4.5 mil to about 7 mil.

2. The sterilization process test device of claim 1, wherein each of the at least one hole is defined by a circular shaped opening having a diameter of less than 0.1 inches.

3. The sterilization process test device of claim 2, wherein each of the at least one hole is defined by a circular shaped opening having a diameter of about 1/16 inches to about 3/32 inches.

4. The sterilization process test device of claim 1, wherein the at least one hole includes a single hole defined by a circular shaped opening having a diameter of about 1/16 inches.

5. The sterilization process test device of claim 1, wherein the at least one hole includes two holes, each defined by a circular shaped opening having a diameter of about 1/16 inches.

6. The sterilization process test device of claim 1, wherein the at least one hole includes four holes, each defined by a circular shaped opening having a diameter of about 1/16 inches.

7. The sterilization process test device of claim 1, wherein the at least one hole includes one hole defined by a circular shaped opening having a diameter of about 3/32 inches.

8. A sterilization process test device, comprising:
a body including a chamber configured to contain at least one sterilization indicator, an inlet opening configured to receive the at least one sterilization indicator, and at least one hole, wherein each of the at least one hole is defined by an opening extending through a thickness of the body;
a cap configured to engage the body to sealingly close the inlet opening; and
a steam and gas permeable cover arranged over the at least one hole and attached to an outer surface of the body surrounding the at least one hole;
wherein the only fluid communication between the chamber and an external environment is provided through the steam and gas permeable cover and the at least one hole,
wherein the steam and gas permeable cover is formed from an autoclave tape comprising a crepe paper substrate and an adhesive layer, wherein the autoclave tape has a total thickness of about 5.5 mil to about 6 mil.

9. The sterilization process test device of claim 1, wherein the cap is formed from silicone.

10. The sterilization process test device of claim 1, wherein the body has a tubular shape and configured to withstand heat and vacuum pressure during a steam sterilization process.

11. The sterilization process test device of claim 1, wherein the body is a tubular body formed from polycarbonate and having a thickness of about 1/16 inches to about 1/4 inches.

12. The sterilization process test device of claim 11, wherein the body is a tubular body formed from polycarbonate and having an outer diameter of about 3/4 inches, an inner diameter of about 5/8 inches, and a length of about 3.75 inches.

13. The sterilization process test device of claim 1, wherein the at least one sterilization indicator includes a biological indicator and a chemical indicator.

* * * * *